United States Patent [19]

Goto et al.

[11] Patent Number: 4,581,155

[45] Date of Patent: Apr. 8, 1986

[54] HALOGENOPYRIMIDINE DERIVATIVES

[75] Inventors: Yasuyuki Goto; Tetsuya Ogawa; Kisei Kitano; Masahiro Fukui, all of Yokohamashi; Shigeru Sugimori, Fujisawashi, all of Japan

[73] Assignee: Chisso Corporation, Osaka, Japan

[21] Appl. No.: 593,434

[22] Filed: Mar. 26, 1984

[30] Foreign Application Priority Data

Mar. 31, 1983 [JP] Japan .................. 58-56692
May 24, 1983 [JP] Japan .................. 58-91148
Sep. 1, 1983 [JP] Japan .................. 58-160671

[51] Int. Cl.$^4$ .......... C09K 3/34; G02F 1/13; C07D 239/02
[52] U.S. Cl. .............. 252/299.61; 252/299.5; 350/350 R; 544/242; 544/335
[58] Field of Search ............ 252/299.61, 299.5; 350/350 R; 544/335, 242

[56] References Cited

U.S. PATENT DOCUMENTS 3,997,536 12/1976 Boller et al. ................ 252/229.61
4,062,798 12/1977 Boller et al. ................ 252/299.61
4,273,929 6/1981 Boller et al. ................ 252/299.61
4,309,539 1/1982 Boller et al. ................ 252/299.61
4,324,455 4/1982 Imahori et al. .............. 252/299.1
4,402,849 9/1983 Krause et al. ............... 252/299.61

FOREIGN PATENT DOCUMENTS 2257588 6/1973 Fed. Rep. of Germany ................ 252/299.61
55-152777 11/1980 Japan ................ 252/299.61

OTHER PUBLICATIONS

Boller, A., et al., Mol. Cryst. Liq. Cryst., vol. 42, No. 1-3, pp. 215-231, (1977).

*Primary Examiner*—Teddy S. Gron
*Attorney, Agent, or Firm*—Fred Philpitt

[57] ABSTRACT

Novel compounds capable of improving various characteristics required for liquid crystal compositions when added to liquid crystal substances, and liquid crystal compositions containing the same are provided, which novel compounds are halogenopyrimidine derivatives expressed by the general formula

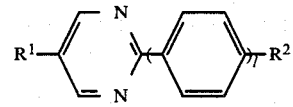

wherein $R^1$ represents an alkyl group of 1 to 10 carbon atoms, $R^2$ represents a halogen atom of F, Cl of Br and l represents 1 or 2.

6 Claims, No Drawings

HALOGENOPYRIMIDINE DERIVATIVES

BACKGROUND OF THE INVENTION

This invention relates to novel compounds as a component of liquid crystal mixtures and liquid crystal compositions containing the same.

Liquid crystal display elements utilize the optical anisotropy and the dielectric anisotropy of liquid crystal substances, and are classified into those of various modes such as TN type (twisted nematic type), DS type (dynamic scattering type), guest-host type, DAP type, etc. depending on their display modes, and the properties of liquid crystal substances suitable to the respective uses vary. It is common to any of liquid crystal substances that they are stable to moisture, air, heat, light, etc., and those having a mesomorphic range as broad as possible, around room temperature, have been sought. Up to the present, however, any single compound which satisfies such conditions has not been found; hence liquid crystal compositions obtained by blending several kinds of liquid crystal compounds and non-liquid crystal compounds have been used.

Namely it has generally been required for liquid crystal compositions used for display elements that not only they should have a broad mesomorphic range including practical temperatures, but also they should have low viscosities, and further they should impart to display devices, low threshold voltages, short response times, and small electric power consumption.

British Pat. No. 1,473,990 discloses 5-alkyl-2-(4-cyanophenyl)pyrimidines as liquid crystal compounds having a great dielectric anisotropy, but even these compounds do not satisfy all of the above conditions required as a material for liquid crystal display elements.

The object of the present invention is to provide novel compounds which, when added to liquid crystal substances, can improve some characteristics required for the resulting liquid crystal compositions.

SUMMARY OF THE INVENTION

The present invention resides in
(1) as a first aspect, halogenopyrimidine derivatives expressed by the general formula

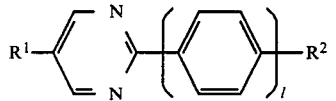
(I)

wherein $R^1$ represents an alkyl group of 1 to 10 carbon atoms, $R^2$ represents a halogen atom of F, Cl or Br and l represents 1 or 2.

Further the invention has the following embodiments (2) to (5):

(2) 5-Alkyl-2-(4-halogenophenyl)pyrimidines expressed by the general formula (I) of the above item (1) wherein l represents 1 and $R^1$ represents a linear chain alkyl group of 1 to 8 carbon atoms.

(3) 5-Alkyl-2-(4'-halogenobiphenylyl-4)pyrimidines expressed by the general formula (I) of the above item (1) wherein l represents 2 and $R^1$ represents a linear chain alkyl group of 1 to 8 carbon atoms.

(4) 5-Alkyl-2-(4-fluorophenyl)pyrimidines expressed by the general formula (I) of the above item (1) wherein l represents 1, $R^1$ represents a linear chain alkyl group of 1 to 8 carbon atoms and $R^2$ represents F atom.

(5) 5-Alkyl-2-(4'-fluorobiphenylyl-4-)-pyrimidines expressed by the general formula (I) of the above item (1) wherein l represents 2, $R^1$ represents a linear chain alkyl group of 1 to 8 carbon atoms and $R^2$ represents F atom.

As a second aspect, the present invention resides in liquid crystal compositions containing halogenopyrimidines expressed by the general formula (I) defined above.

DETAILED DESCRIPTION OF THE INVENTION

Groups of compounds of the present invention are 5-alkyl-2-(4-halogenophenyl) pyrimidines and 5-alkyl-2-(4'-halogenobiphenylyl-4)pyrimdines.

Preferred embodiments of the present invention are compounds expressed by the formula (I) wherein $R^1$ represents an alkyl group of 1 to 8 carbon atoms, and more preferred embodiments thereof are 5-alkyl-2-(4-fluorophenyl)pyrimidines and 5-alkyl-2-(4'-fluorobiphenylyl-4)-pyrimidines expressed by the formula (I) wherein $R^2$ is F atom.

5-Alkyl-2-(4-halogenophenyl)pyrimidines wherein the alkyl group has carbon atoms greater than 10 are undesirable since their effectiveness as a viscosity-reducing agent is small. Further, 5-alkyl-2-(4'-halogenobiphenylyl-4)pyrimidines wherein the alkyl group has long chain carbon atoms are not practical due to their high viscosity.

Compounds of the present invention expressed by the formula (I) wherein l represents 2 have a large positive value of dielectric anisotropy (abbreviate to $\Delta\epsilon$; $\Delta\epsilon = \epsilon_\parallel - \epsilon_\perp$ wherein $\epsilon_\parallel$ represents a parallel dielectric constant and $\epsilon_\perp$ represents a perpendicular dielectric constant, and their $\Delta\epsilon$ values are about +22.

Compounds of the present invention expressed by the formula (I) wherein l represents 1 have extrapolation values of $\Delta\epsilon$ (extrapolation values from observed values of mixtures thereof with liquid crystal compositions of trans-cyclohexane derivatives) as considerably large as about +14.

Compounds of the present invention have low viscosities. Particularly those of the formula (I) wherein l represents 1 and $R^2$ represents F have extrapolation values of viscosity at 20° C. (extrapolation values at 20° C. of mixtures thereof with liquid crystal compositions of trans-cyclohexane derivatives) as extremely low as 6 to 8 cp.

Due to the above-mentioned specific properties, when the compounds of the present invention are added as a component, an effectiveness of reducing the viscosites of the resulting liquid crystal compositions and an effectiveness of reducing the threshold voltage of liquid crystal display elements obtained by the use of the compositions and improving the response velocity thereof are remarkable.

Further, the compounds of the present invention expressed by the formula (I) wherein l represents 2 have an anisotropy of refractive index $\Delta n$ of about 0.24 which is larger than those of known liquid crystal substances; thus when the compounds are used in a small amount, it is possible to obtain display elements having a superior contrast.

5-Alkyl-2-(4'-halogenobiphenylyl-4)pyrimidines of the present invention have high clearing points; thus they, when added, have an effectiveness of raising the clearing points of the resulting liquid crystal compositions.

Further the compounds of the present invention are stable; hence when they are used as a structural element of liquid crystal display elements, they are very advantageous. Still further the compounds of the present invention have a superior compatibility; hence when they are blended with other nematic liquid crystals and liquid crystal compositions such as those of cyclohexanecarboxylic acid phenyl esters, benzoic acid phenyl esters, phenylmetadioxanes, cyclohexanecarboxylic acid cyclohexyl esters, Schiff's bases, azoxy compounds, etc., it is possible to notably improve the specific properties of the resulting liquid crystal compositions, as described above.

The compounds of the present invention having such superior specific properties are prepared according to the following reactions:

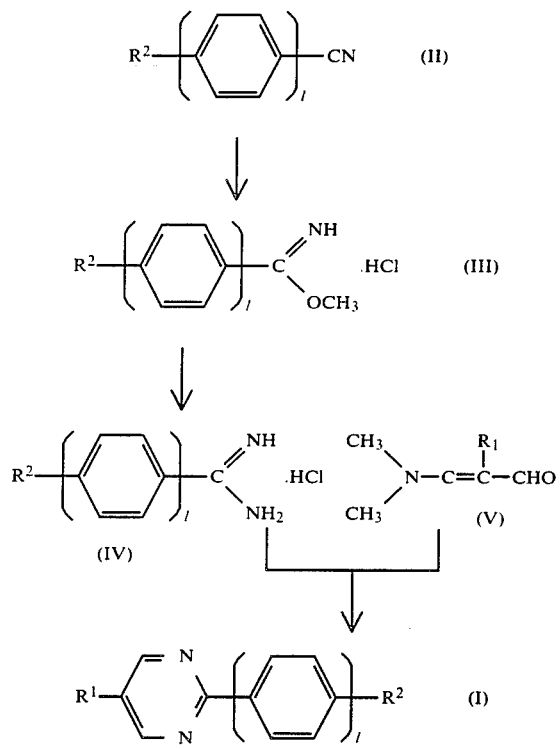

In the above formulas, $R^1$, $R^2$ and $l$ are as defined above.

First, a 4-halogenobenzonitrile or 4-halogeno-4'-cyanobiphenylyl (compound (II)) as a starting raw material is reacted with HCl gas in methyl alcohol solvent to obtain an imido ether hydrochloride derivative (compound (III)), which is then reacted with $NH_3$ gas in an alcohol solvent to obtain an amidine hydrochloride derivative (compound (IV)), which is then subjected to condensation-cyclization reaction with an acrolein derivative (compound (V)) in the presence of a suitable basic catalyst such as metal alcoholate, NaOH, DBU (1,8-diazabicyclo[5.4.0]-7-undecene), etc. to obtain the objective compound (I).

Preparation of the compounds (I) of the present invention and use examples thereof will be described below by way of Examples.

EXAMPLE 1

Preparation of 5-propyl-2-(4-fluorophenyl)pyrimidine

To a sodium methylate solution under agitation obtained by dissolving Na (2.8 g, 0.12 mol) in anhydrous methanol (20 c.c.) was added 4-fluorobenzamidine hydrochloride (10.5 g, 0.06 mol), followed by adding α-propyl-β-dimethylaminoacrolein (9.2 g, 0.06 mol), thereafter refluxing on heating for 3 hours with stirring, distilling off methanol under the atmospheric pressure after completion of the reaction, adding toluene (20cc) to the reaction residue to extract the resulting product, washing the extraction liquid with water, drying with anhydrous sodium sulfate, distilling off toluene and recrystallizing the remaining oily substance from ethanol (20 c.c.) to obtain the objective 5-propyl-2-(4-fluorophenyl)pyrimidine (7.0 g). Yield: 55%. M.P. 52.7° C.

EXAMPLES 2~21

Example 1 was repeated except that 4-fluorobenzamidine hydrochloride and α-propyl-β-dimethylaminoacrolein of Example 1 were replaced by other substituted benzamidine hydrochlorides and α-alkyl-β-dimethylaminoacroleins, to prepare compounds shown in Examples 2~21 of Table 1. The values of physical properties thereof are shown in Table 1 together with the results of Example 1.

TABLE 1

| Example | $l$ in formula (I) | $R^1$ in formula (I) | $R^2$ in formula (I) | Phase transition temperature (°C.) | | | |
|---|---|---|---|---|---|---|---|
| | | | | C | S | N | I |
| 1 | 1 | $C_3H_7$ | F | . 52.7 | | | . |
| 2 | 1 | $C_2H_5$ | F | . 61.6 | | | . |
| 3 | 1 | $C_4H_9$ | F | . 41.3 | | | . |
| 4 | 1 | $C_5H_{11}$ | F | . 28.9 | | | . |
| 5 | 1 | $C_6H_{13}$ | F | . 38.8 | | | . |
| 6 | 1 | $C_7H_{15}$ | F | . 28.6 | | | . |
| 7 | 1 | $C_2H_5$ | Cl | . 84.8 | | .*(7.3) | . |
| 8 | 1 | $C_3H_7$ | Cl | . 99.4 | | .*(7.5) | . |
| 9 | 1 | $C_4H_9$ | Cl | . 50.9 | | .*(2.0) | . |
| 10 | 1 | $C_5H_{11}$ | Cl | . 53.5 | | .*(5.3) | . |
| 11 | 1 | $C_6H_{13}$ | Cl | . 56.6 | | .*(6.7) | . |
| 12 | 1 | $C_3H_7$ | Br | . 106.5 | | .*(24.0) | . |
| 13 | 1 | $C_4H_9$ | Br | . 54.3 | | .*(15.3) | . |
| 14 | 1 | $C_5H_{11}$ | Br | . 59.0 | | .*(26.7) | . |
| 15 | 1 | $C_6H_{13}$ | Br | . 59.8 | | .*(19.3) | . |
| 16 | 2 | $C_3H_7$ | F | . 96.9 | | .177.4 | . |
| 17 | 2 | $C_2H_5$ | F | . 100.8 | | .166.6 | . |
| 18 | 2 | $C_4H_9$ | F | . 90.6 | | .162.0 | . |
| 19 | 2 | $C_5H_{11}$ | F | . 88.1 | .103.3 | .167.6 | . |
| 20 | 2 | $C_6H_{13}$ | F | . 90.6 | .126.5 | .157.0 | . |
| 21 | 2 | $C_7H_{15}$ | F | . 104.1 | .140.6 | .158.3 | . |

In Table 1, the symbols C, S, N and I represent the respective phases of crystal, smectic, nematic and isotropic liquids, and numeral figures following the symbol. represent transition points (°C.) from the above phases to the right side phases. Further, the numerals inside *( ) are values obtained by blending the compounds with a liquid crystal composition (a composition consisting of three compounds in Application example 2 described later) followed by extrapolation.

APPLICATION EXAMPLE 1

A liquid crystal composition consisting of
trans-4-propyl-(4'-cyanophenyl)cyclohexane 26% by weight,
trans-4-pentyl-(4'-cyanophenyl)cyclohexane 36% by weight, trans-4-heptyl-(4'-cyanophenyl)cyclohexane 25% by weight and trans-4-pentyl-(4"-cyanobiphenylyl-4)cyclohexane 13% by weight, has a nematic mesomorphic range of −5° C. to 71.9° C. When this liquid crystal composition was sealed in a TN cell of 10 μm thick, the threshold voltage and saturation voltage of the resulting cell were 1.84 V and 2.43 V, respectively. Further, its viscosity was 27.9 cp at 20° C.

When 5-propyl-2-(4-fluorophenyl)pyrimidine (15 parts by weight) of Example 1 as one of the compounds of the present invention was added to the above liquid crystal composition (85 parts by weight), the resulting liquid crystal composition had a mesomorphic range of −10° to 55° C.; hence the temperature region on the lower temperature side was improved, and when the composition was sealed in the same TN cell of 10 μm thick as above, the threshold voltage and saturation voltage of the resulting cell were reduced down to 1.30 V and 1.83 V, respectively, and its viscosity was 23 cp at 20° C., that is, improved to a large extent.

APPLICATION EXAMPLE 2

A liquid crystal composition consisting of trans-4-propyl-(4'-cyanophenyl)cyclohexane 30% by weight, trans-4-pentyl-(4'-cyanophenyl)cyclohexane 40% by weight, and trans-4-heptyl-(4'-cyanophenyl)cyclohexane 30% by weight, has a N-I point of 52.1° C. When this composition was sealed in a TN cell of 10 μm thick, the threshold voltage and saturation voltage of the resulting cell were 1.55 V and 2.15 V, respectively.

When 5-propyl-2-(4'-fluorobiphenylyl-4)pyrimidine (15 parts by weight) of Example 16 as one of the compounds of the present invention was added to the above liquid crystal composition (85 parts by weight), the resulting nematic liquid crystal composition had a N-I point of 65° C. When this liquid crystal composition was sealed in the above TN cell, the threshold voltage and saturation voltage of the resulting cell were 1.41 V and 1.90 V, respectively. This indicates that when the compound of the present invention is added, the clearing point is raised and the operation voltages are reduced.

As described above, when the compounds of the present invention are used, the characteristics of the resulting liquid crystal compositions can be improved; hence their effectiveness is notable.

What we claim is:

1. A pyrimidine derivative expressed by the formula

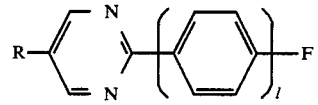

wherein R represents an alkyl group of 1 to 10 carbon atoms and $l$ represents 1 or 2.

2. A 5-alkyl-2-(4-fluorophenyl)pyrimidine according to claim 1 wherein R represents methyl, ethyl, propyl, butyl, pentyl, hexyl, heptyl or octyl group.

3. A 5-alkyl-2-(4'-fluorobiphenylyl-4)pyrimidine according to claim 1 wherein R represents methyl, ethyl, propyl, butyl, pentyl, hexyl, heptyl or octyl group.

4. A liquid crystal composition comprising at least two components at least one of which is a pyrimidine derivative expressed by the formula

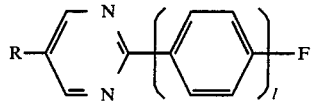

wherein R represents an alkyl group of 1 to 10 carbon atoms and $l$ represents 1 to 2.

5. A composition according to claim 4 wherein said derivative is a 5-alkyl-2-(4-fluorophenyl)pyrimidine wherein R represents methyl, ethyl, propyl, butyl, pentyl, hexyl, heptyl or octyl group.

6. A composition according to claim 4 wherein said derivative is a 5-alkyl-2-(4'-fluorobiphenylyl-4)pyrimidine according to claim 7 wherein R represents methyl, ethyl, propyl, butyl, pentyl, hexyl, heptyl or octyl group.

* * * * *